United States Patent [19]

Saito et al.

[11] Patent Number: 5,594,545
[45] Date of Patent: Jan. 14, 1997

[54] MICROFLOW CELL

[75] Inventors: Muneo Saito, Hachioji; Yasuyuki Kurosu, Tachikawa; Toru Sasaki, Hachioji, all of Japan

[73] Assignee: Nihon Bunko Kabushiki Kaisha, Hachioji, Japan

[21] Appl. No.: 306,523

[22] Filed: Nov. 17, 1994

Related U.S. Application Data

[63] Continuation of Ser. No. 958,473, Oct. 8, 1992, abandoned, which is a continuation of Ser. No. 688,107, Apr. 19, 1991, abandoned.

[30] Foreign Application Priority Data

Sep. 5, 1990 [JP] Japan .................................. 2-236031

[51] Int. Cl.$^6$ .................................................. G01N 1/10
[52] U.S. Cl. ........................ 356/246; 356/440; 204/600
[58] Field of Search ............................. 356/244, 246, 356/344, 336, 338, 44, 133, 335, 337, 339–343; 250/574, 576; 204/299 R, 180.1, 183.3

[56] References Cited

U.S. PATENT DOCUMENTS

| | | | |
|---|---|---|---|
| 2,999,414 | 9/1961 | Stamm et al. | 356/339 |
| 3,342,099 | 9/1967 | Kaye | 356/340 |
| 3,523,738 | 8/1970 | Chisholm | 356/440 |
| 3,529,896 | 9/1970 | Padawer | 356/246 |
| 4,348,107 | 9/1982 | Leif | 356/246 |
| 4,521,521 | 6/1985 | Abbott et al. | 356/336 |
| 5,017,008 | 5/1991 | Akiyama | 356/336 |
| 5,047,963 | 9/1991 | Kosaka | 356/339 |

OTHER PUBLICATIONS

Review of Scientific Instruments, vol. 55, No. 9, Sep. 1984; pp. 1375–1400; J. A. Steinkamp; "Flow Cytometry".
HRC Journal of High Resolution Chromatography, vol. 14, No. 3, Mar. 1991; pp. 186–190, Kurosu, et al.; "Fluorescence Detection With An Immersed Flow Cell In Capillary Electrophoresis".
Analytical Chemistry, vol. 60, No. 17, Sep. 1988, pp. 1832–1834; Kuhr, et al.; "Indirect Fluorescence Detection of Native Amino Acids In Capillary Zone Electrophoresis".
Journal of Chromatography, vol. 502, 1990; pp. 247–255; L. Hernandez, et al.; "Detection and Quantification of Capillary Electrophoresis Zones By Fluoescence Microscopy".
Analytical Chemsitry, vol. 62, No. 5, Mar. 1990, pp. 496–503; Cheng, et al.; "Interaction of Capillary Zone Electrophoresis With a Sheath Flow Flor Cuvette Detector".
"Review of Scientific Instruments", vol. 55, No. 9, Sep. 1994; pp. 1375–1400;.
"HRC Journal of High Resolution Chromatography", vol. 14, No. 3, Mar. 1991, pp. 186–190;.
"Analytical Chemistry", vol. 60, No. 17, Sep. 1988, pp. 1832–1834;.
"Journal of Chromatography" vol. 502, 1990 pp. 247–255;.
"Analytical Chemistry", vol. 62, No. 5, Mar. 1990, pp. 496–503;.
"Journal of Chromatography", vol. 480, 1989, pp. 141–155.

*Primary Examiner*—Hoa Q. Pham
*Attorney, Agent, or Firm*—Ronald R. Snider

[57] ABSTRACT

A microflow cell comprising an outer cylinder disposed on the outer periphery of a cylindrical flow cell and having a flat surface on at least a light-entering surface, and a filling material inserted between the outer cylinder and the flow cell and a capillary electrophoresis method using such a microflow cell. Since the outer cylinder is provided on the outer periphery of the cylindrical flow cell and the gap between the flow cell and the outer cylinder is filled up with a filling liquid, the quantity of scattered light is reduced, thereby enabling the adoption of fluorometry in the analysis of capillary electrophoresis.

24 Claims, 7 Drawing Sheets

MICROFLOW CELL

This application is a continuation of application Ser. No. 07/958,478, filed Oct. 8, 1992 now abandoned; which is a continuation of application Ser. No. 07/688,107, filed Apr. 19, 1991 now abandoned.

BACKGROUND OF THE INVENTION

1. Field of the Invention

The present invention relates to a microflow cell and, more particularly, to the improvement of a micro flow cell for analyzing the sample in the cell by an optional means.

2. Description of the Prior Art

Microflow cells are now used in various fields of analysis and separation.

For example, in capillary electrophoresis (CE), a capillary tube having an inner diameter of about 50 µm is used, and a part of the capillary (fused silica) tube can be used as a flow cell. In order to analyze the sample in the flow cell, an ultraviolet light (UV) absorbance detector is widely used by virtue of its simple structure.

Use of a fluorescence detector for the analysis of the sample in the capillary tube has been groped. Although the method of adopting fluorescence detection enables the analysis with higher selecting and sensitivity, very few reports has hitherto been made on this method.

This is ascribed to the fact that since a general capillary electrophoresis tube has an inner diameter of not more than 50 µm, a small cell corresponding to the tube is required.

That is, the intensity of the scatted light of the excitation light by the flow cell becomes so high as to inconveniently raise the level of the background signal and the noise.

Several methods have been proposed to solve this problem. For example, Green and his co-worker and Cheng and his co-worker use a sheathed cuvette flow chamber and Fernandez and his co-worker use a fluorescence microscope.

Among these, some practical reports have been made on laser-excited fluorescence detection. Kerr and Jeung suggest that indirect fluorescence detection is useful in capillary electrophoresis. Since a laser beam is suitable for focussing light beam and can be projected to the small inner diameter of a fused silica capillary in the form of a small spot, it is possible to suppress the increase in background signal and noise caused by scattered light.

However, use of a laser as a light exciting source for the fluorescence measurement of capillary electrophoresis has some problems. For example, it makes the continuous change of the exciting wavelength impossible, it involves a high cost and the laser has a large size in comparison with the capillary electrophoresis separation system itself.

If use of a general fluorescence detector for HPLC is possible, it is very convenient because change of exciting wavelength is easy. In addition, the cost of the detection mechanism is lower than that of the system using a microscope or a laser.

However, it is very difficult to obtain a projection spot of not more than 50 µm by an incoherent light beam. It is also difficult to reduce the noise level caused by the scattering of the light exiting by a small flow cell.

SUMMARY OF THE INVENTION

Accordingly, it is an object of the present invention to eliminate the above-described problems in the prior art and to provide a microflow cell which is capable of analysis with a high sensitivity and a high accuracy by the use of a general-purpose fluorescence detector.

To achieve this aim, the present invention provides a microflow cell comprising: an outer cylinder disposed on the outer periphery of a cylindrical flow cell and having a flat surface on at least a light-entering surface; and filling material inserted between the outer cylinder and the flow cell.

The surface adjacent to the light-entering surface is preferably concentric with the flow cell. That is a circular flow cell will have a concentric emitting surface 130b as shown in FIG. 11.

The filling material is preferably a liquid having substantially the same refractive index as the flow cell and the outer cylinder.

The filling material is preferably one selected from the group consisting of ethanol, 1-propanal and dichrolomethane.

It is preferable that the analysis adopting a capillary electrophoresis method is carried out by fluoremetry using such a microflow cell.

By adopting such a capillary electrophoresis method, it is also possible to measure a fluorescence spectrum.

A microflow cell according to the present invention, which has an outer cylinder, as described above, can collect light on one surface of the outer cylinder with comparative easiness. In addition, even if the spot of the excited light flux is slightly larger than the inner diameter of the flow cell, since the incident angle of the excited light flux with respect to the outer cylinder is constantly 0 degree, namely, the excited light flux is perpendicular to the flat surface, scattered light is unlikely to be caused.

Since the gap between the outer cylinder and the cylindrical flow cell is filled up with a filling liquid having substantially the same refractive index as the flow cell, it is possible to suppress the generation of scattered light without impairing the rectilinear propagation of the excited light and fluorescence emitting light.

That is, the differences in refractive index on the optical boundaries between the outer cylinder and the filling liquid and, filling liquid and flow cell which the excited light flux passes, and the differences in refractive index on the optical boundaries between the flow cell and the filling liquid and, the filling liquid and the outer cylinder which the fluorescence emitting light passes become minimum, thereby reducing scattering.

If the emitting surface of fluorescence emitting light is also a flat surface, it is possible to reduce the scattering light at the time emission to the minimum.

The above and other objective, features and advantages of the present invention will become clear from the following description of the preferred embodiments thereof, taken in conjunction with accompanying drawing.

DESCRIPTION OF THE PREFERRED EMBODIMENTS

Preferred embodiments of the present invention will be explained hereinunder with reference to the accompanying drawings.

Figure 1:
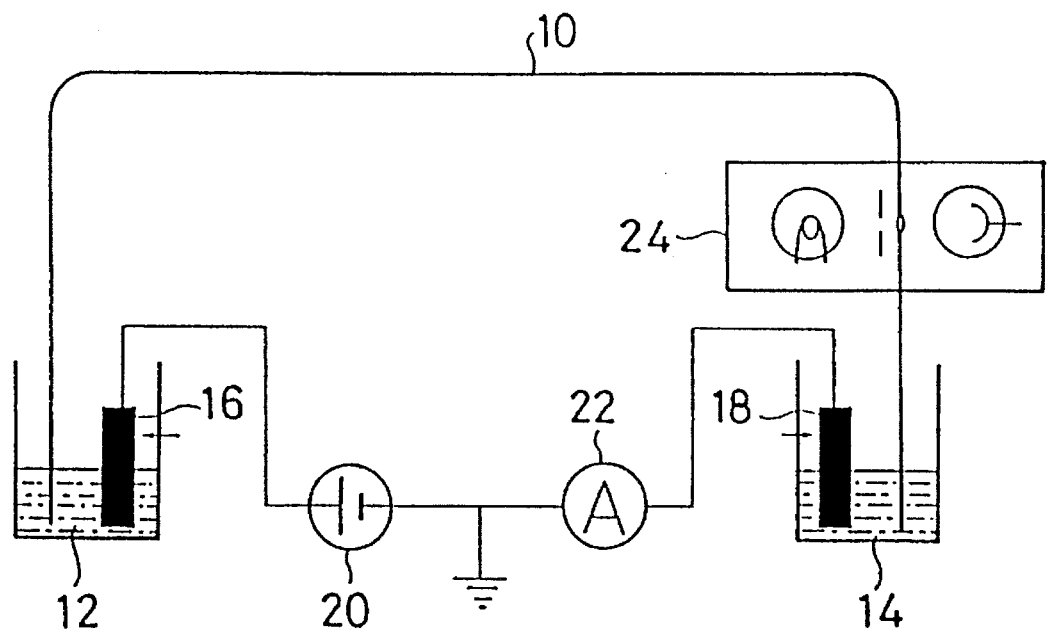
FIG. 1 is an explanatory view of a capillary electrophoresis apparatus to which the present invention is applied.

FIG. 1 schematically shows a capillary electrophoresis apparatus to which a microflow cell according to the present invention is applied.

In FIG. 1, both ends of a fused silica tube 10 which constitutes a capillary are electrically connected to platinum electrodes 16 and 18 through electrolytes 12 and 14, respectively. A high voltage (e.g.,the maximum output: 30 kV, 100 μA) is applied to the platinum electrodes 16, 18 from a high-voltage power source 20. The current flow thereof can be monitored by an ammeter 22. A fluorescence detector 24 is provided at the fused silica tube 10. In this way, the substance separated in the fused silica tube 10 is detected by the fluorescence detector 24.

Figure 2:
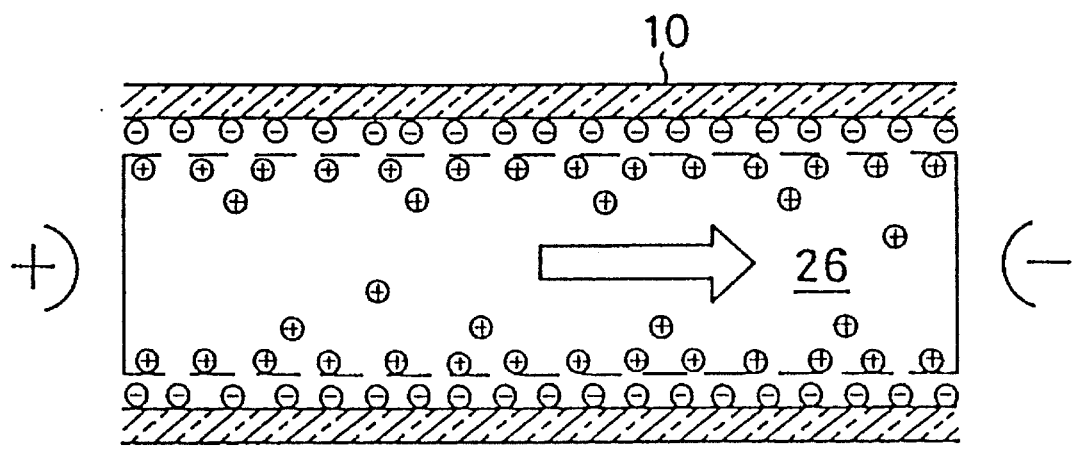
FIG. 2 is an explanatory view of the mechanism of capillary electrophoresis.

Separation in the fused silica tube 10 is carried out in such a manner as is shown in FIG. 2.

In FIG. 2, the inner surface of the fused silica tube 10 has negative charges. Therefore, the liquid in the fused silica tube 10 has the same amount of positive charges as the amount of negative charges on the inner surface so as to neutralize the negative charges on the inner surface. Many of the positive charges are attracted to the negative charges on the inner surface, thereby forming an electric double layer.

Therefore, when an electric field is applied to both ends of the fused silica tube 10, the sample liquid having the positive charges is attracted to the direction of a negative pole, and the liquid is integrally moved as a whole. This is a flow of electroendosemosis in capillary electrophoresis. A liquid flow is ordinarily caused by a flow of electroendosemosis simultaneously with electrophoresis.

In this embodiment, a part of the capillary (fused silica) tube 10 is used as a flow cell for fluorescence detection so as to detect the substance separated by capillary electrophoresis as it is.

A microflow cell as the flow cell now be explained.

MICROFLOW CELL

In the case of using the capillary separation tube 10 as a flow cell as it is, as described above, the following problem is brought about.

Generally, when light enters obliquely to an optical boundary the refractive index of which abruptly changes, the light is refracted and the incident angle changes.

For example, in the case of a boundary between media having refractive indices of $n_1$ and $n_2$, the total refractive index R is represented by the following equation:

$$R = \frac{1}{2} \left[ \frac{\sin^2(\phi - \phi')}{\sin^2(\phi + \phi')} + \frac{\tan^2(\phi - \phi')}{\tan^2(\phi + \phi')} \right]$$

$$\text{wherein } \frac{\sin\phi}{\sin\phi'} = \frac{n_2}{n_1}$$

In fluorescence detection using a flow cell, such a boundary exists at four portions, namely, between air and the silica (the component of the cell 10), the silica and the liquid, the liquid and the silica, and the silica and air.

Among these, on the boundaries between a portion having a low refractive index and a portion having a high refractive index, if the incident angle exceeds the critical angle $\phi_c = \sin^{-1}(n_1/n_2)$, total reflection and multiple reflection are caused as scattering of the light, resulting in the increase in background signal and the deterioration of the sensitivity of fluorescence detection.

Such boundaries exist between silica and the sample liquid, and the silica and air, which cause internal reflection in the flow cell.

Figure 3:
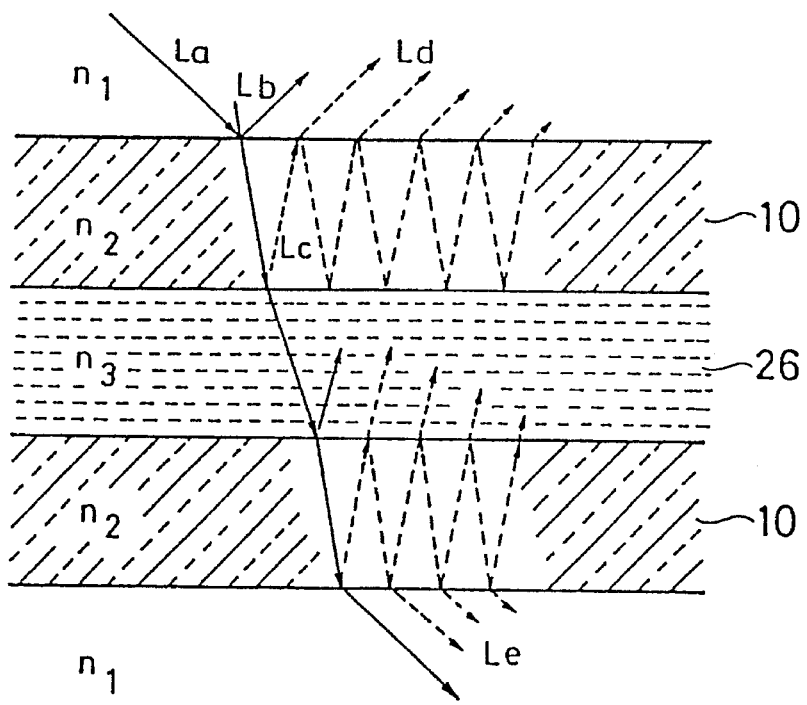
FIG. 3 is an explanatory view of the scattered light caused at the time of fluorometry in capillary electrophoresis apparatus.

FIG. 3 schematically shows the reflection on such boundaries. The differences in the refractive index on the first boundary is about 0.1 and that on the second boundary is about 1.4.

As is obvious from FIG. 3, when light La enters the fused silica tube 10 from air (having a refractive index of $n_1$) and into tube 10 (having a refractive index of $n_2$), a slight quantity of reflected light Lb is generated but most of the light La is refracted as it is and proceeds to the interior of the silica tube 10.

When the light La enters a sample liquid 26 (having a refractive index of $n_3$) from the silica tube 10, the light La is reflected on the boundary and the reflected light Lc is repeatedly reflected by the wall of the silica tube 10, thereby emitting scattered light Ld to the outside.

The light which has transmitted the sample liquid 26 proceeds to the opposite wall of the silica tube 10, and when the light exits from the silica tube 10 to the outside (air), reflected light is generated in the same way as described above, thereby emitting scattered light Le. The scattered light Ld and the scattered light Le are main causes for raising the noise level at the time of fluorescence detection.

Adoption of a rectangular flow cell may be considered as a means for minimizing the total reflection and multiple reflection. In this case, the excited light flux enters at right angles relative to the wall of the flow cell. This means that the incident angle is 0 degree. The fluorescence emitting light is taken from the wall adjacent to the wall which the excited light flux enters. In other words, the emitting light is taken at an angle of 90 degrees with respect to the excited light. By this structure, the scattered light based on total reflection and multiple reflection is greatly reduced.

However, in capillary electrophoresis, it is very difficult to make a square flow cell having a small volume which is fit for the diameter of the capillary separation tube. In other words, in the case of using a part of the separation tube as a flow cell by removing a polymer coating in the same ways in UV absorption detection, the flow cell has a section having same configuration as that of the separation tube, namely, a circular section.

Figure 4:
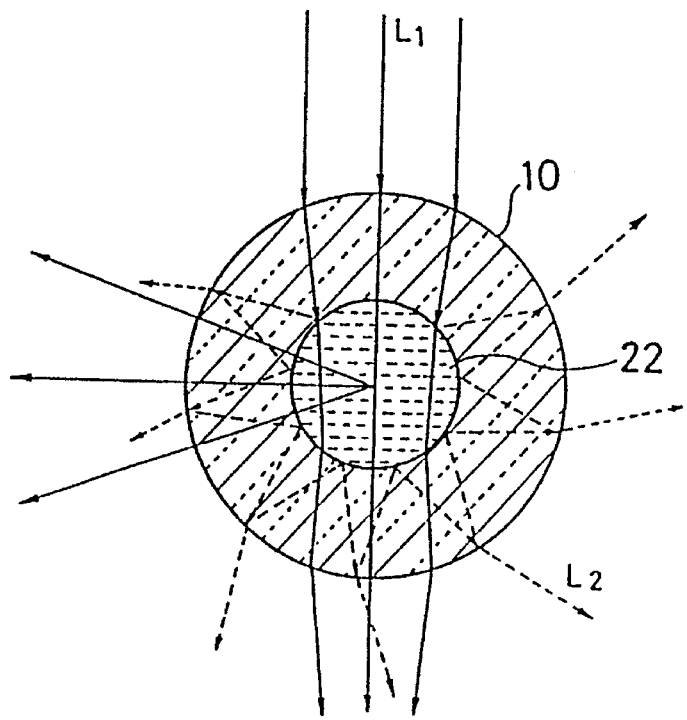
FIG. 4 is an explanatory view of a comparative example of a microflow cell.

FIG. 4 schematically shows the state in which the excited light is scattered in a cylindrical flow cell.

The sample liquid flows in the axial direction of the cylindrical flow cell, namely, in the direction perpendicular to the plane of the drawing. A part of the excited light flux $L_1$ is reflected by the outer wall of the cell which is the boundary between air and the silica. However, the quantity of reflected light is not more than ten and several % of the incident light flux. This is because the boundary is between a portion having a low refractive index and a portion having a high refractive index and the light enters the boundary at an incident angle of approximately 0 degree except for the case skimming over the silica surface. Most of the light passes the boundary and reaches the inner surface of the cell which is the boundary between the silica and the liquid. Although the difference in refractive index is small, this is a boundary between a portion having a low refractive index and a portion having a high refractive index. For this reason, total reflection may be produced on the light which is apart from the center of the beam which has an incident angle of 90 degrees. When the totally reflected light reaches the boundary between the silica and air, it is refracted and proceeds to the boundary between the silica and the liquid. In this way, a part of the totally reflected light causes multiple reflection. When the incident angle at the refracted portion of the multiple reflection is smaller than the critical angle, a part of the light passes through the outer wall of the cell, thereby producing scattered light $L_2$ from the excited light flux in all directions.

The present invention is characterized by the reduction of such scattered light bases on the excited light flux. For this purpose, in this embodiment, a cylindrical capillary separation tube is inserted through a conventional square flow cell for HPLC and the gap between the capillary separation tube and the square flow cell is filled up with a filler liquid having an appropriate refractive index.

Figure 5:
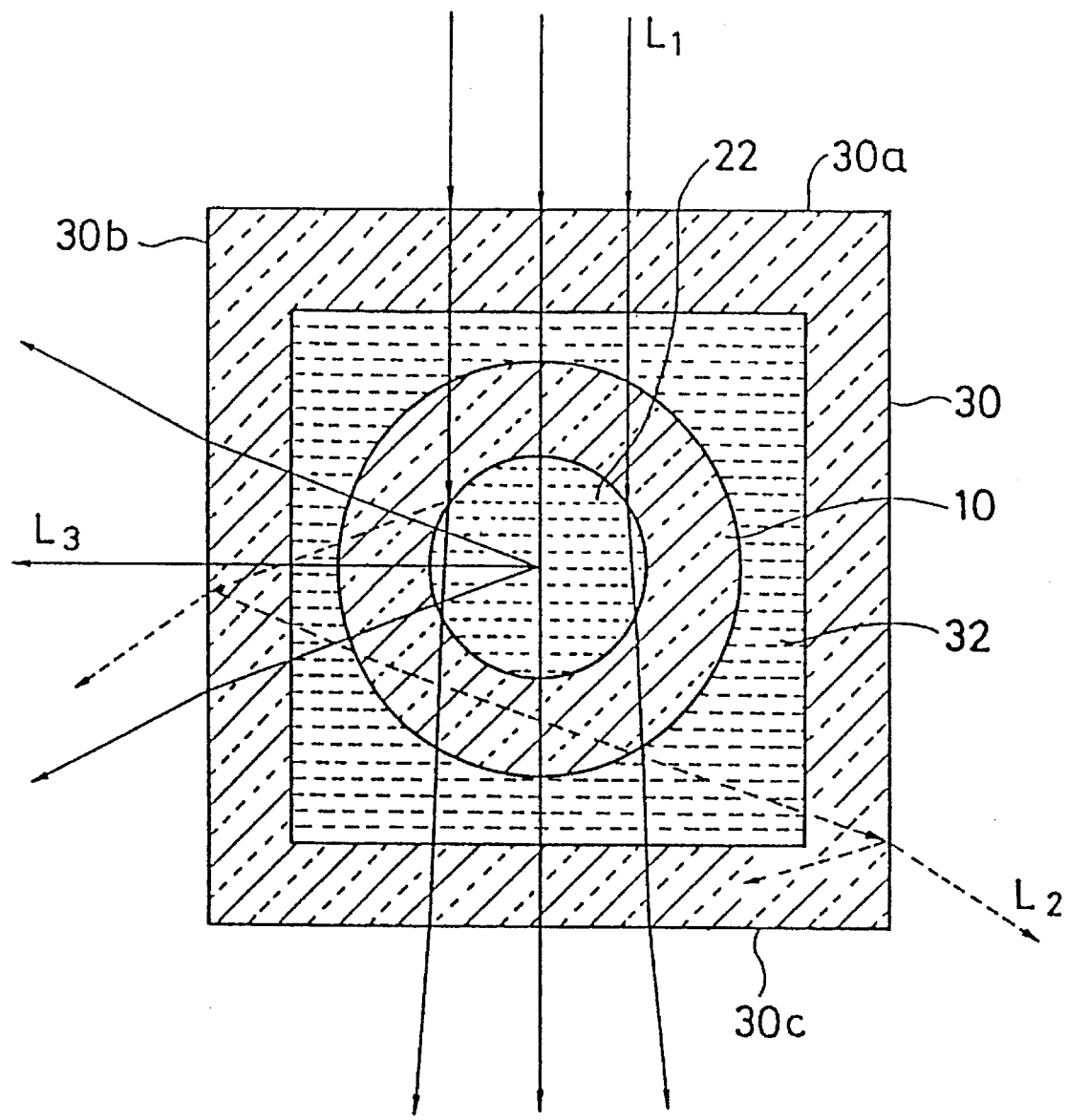
FIG. 5 is an explanatory view of an embodiment of a microflow cell according to the present invention.

The structure of such a flow cell is shown in FIG. 5.

In FIG. 5, a square outer cylinder 30 is provided on the outer periphery of the cylindrical fused silica tube 10. The gap between the silica tube 10 and the square outer cylinder 30 is filled up with a filler liquid 32.

By this structure, the excited light flux $L_1$ enters approximately at right angles, thereby causing almost no scattering on the boundaries between the outer cylinder 30 and the filler liquid 32, and the filler liquid 32 and the silica tube 10. Since the totally reflected light generated on the boundary surface between the silica tube 10 and the filler liquid 32 is emitted to the outside without causing multiple reflection within the wall of the silica tube 10, it is possible to greatly reduce the scattered light $L_2$.

On the other hand, fluorescence emitting light $L_3$ is emitted from the light-emitting surface 30b adjacent to the light-entering surface 30a for the excited light flux $L_1$, and introduced to a desired fluorescence detection system. At this time, the background signal and the noise of fluorescence detection which caused by the scattered light $L_2$ are suppressed to the minimum.

Additionally, since the light-emitting surface 30c for the excited light flux is also a flat surface, it is also possible to prevent the generation of scattered light when the light flux which has passed through the liquid exits from the outer cylinder 30.

Capillary Electrophoresis System

Samples were actually measured by using a microflow cell shown in FIG. 5.

The apparatus used is a capillary electrophoresis system JASCO CE-800. The 870-CE UV/VIS detector, which is a standard detector of this system was removed. A fluorescence detector JASCO 821-FP was attached to the microflow cell 100.

Reagent and Capillary Separation Tube

Quinine and dansyl amino acid produced by Tokyo Kasei Co., Ltd. and Pierce Co., Ltd. (Rockford, U.S.A.), respectively, were used. The other reagents were obtained from Wako Pure Chemical Industries, Ltd. The fused silica capillary (inner diameter: 50 µm, uncoated) was obtained from Gasukuro Kogyo Co., Ltd.

Various factors were investigated under the above-described conditions.

Influence of Refractive Index of Filler Liquid

Figure 6:
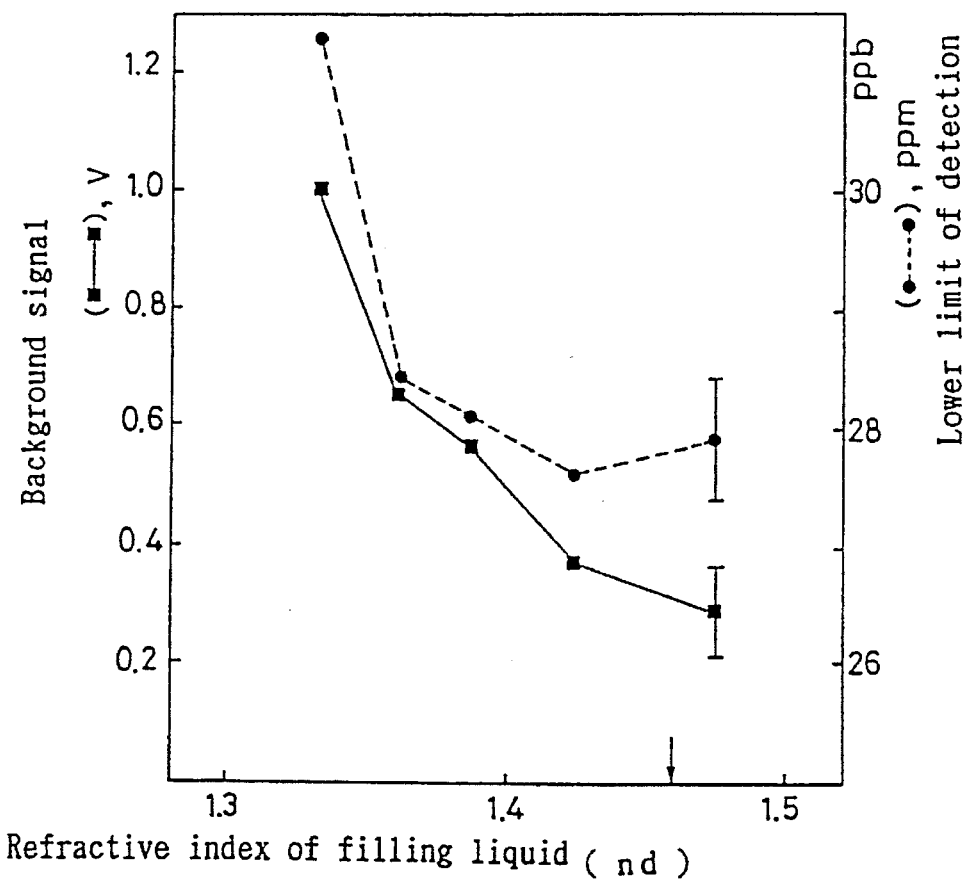
FIG. 6 is an explanatory view of the refractive index of a filling liquid, a background signal and the lower limit of detection.

FIG. 6 shows the influence of the refractive index of the filler liquid 32 on the background level and the lower limit of quinine detection.

As the filler liquid 32, water ($n_d$=1.333 at 20° C.), ethanol ($n_d$=1.361 at 20° C.), 1-propanol ($n_d$=1.387 at 15° C.), dichloromethane ($n_d$=1.424 at 20° C.) and glycerol ($n_d$=1.475 at 15° C.) were used. Various refractive indices were obtained by varying the filler liquid 32.

The capillary had an inner diameter of 50 µm and a length of 300 mm. As the sample liquid 26, 0.1N sulfuric acid solution of quinine was used. Detection was carried out at by projecting excited light having a wavelength of 350 nm and fluorescence emitting light having a wavelength of 460 nm.

As is obvious from FIG. 6, when the refractive index of the filler liquid 26 approaches that of silica, which is a material of the cell 10, the lower limit of detection is lowered. This is obviously ascribed to the small differences in the refractive index between the filler liquid 32 and the outer cylinder 30, and the filler liquid 32 and the flow cell 10. It is when the refractive index of the filler liquid 32 is the closest to that of the silica ($n_d$=1.459 at 18° C.) that the lower limit of detection is the smallest. The error of the measured value caused when glycerol ($n_d$=1.475 at 15° C.) is based on the error of the measuring condition. That is, the viscosity of the filler liquid glycerol is so high that a slight temperature change produces the nonuniformity of the refractive index, so that there is a variation in the measured value.

Since the actual refractive index at a wavelength of 350 nm, which is the wavelength of the excited light, cannot be obtained from literatures, the refractive index $n_d$ at the sodium-line emitting light (15° to 20° C.) is used as a plot.

If there is no filler liquid, the background noise becomes too high for the observation of fluorescence. Any of the filler liquids is usable although there is difference in the maximum value of the lower limit of detection. This means that a little change of the refractive index of a filler liquid does not cancel the effect of the present invention.

In order to facilitate the handling, propanol was used as the filler liquid for the following fluorometry.

Dynamic Range of Detection Responsiveness

Figure 7:
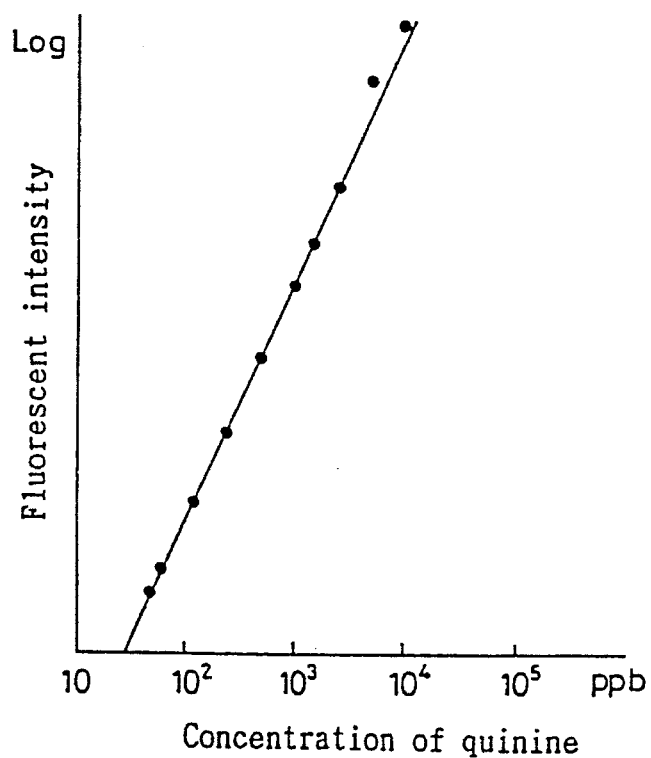
FIG. 7 is a explanatory view showing the relationship between the intensity of fluorescent radiation and the concentration of a sample in the case of using a microflow cell according to the present invention.

FIG. 7 shows the relationship between the intensity of fluorescent radiation and the concentration of quinine.

The lower limit of quinine detection is about 50 ppb at a signal/noise ratio of 2 and the linear dynamic range thereof is not less than several ten ppm. This means that the relationship between the intensity of fluorescent radiation and the concentration of quinine is linear until the concentration becomes about 1,000 times. No filter for restricting the excited light flux is used.

It will be understood that in the case of using a microflow cell of this embodiment, there is an excellent dynamic range which greatly enlarges the applicable concentration range.

Application of Dansyl Amino Acid to Detection

Figure 8:
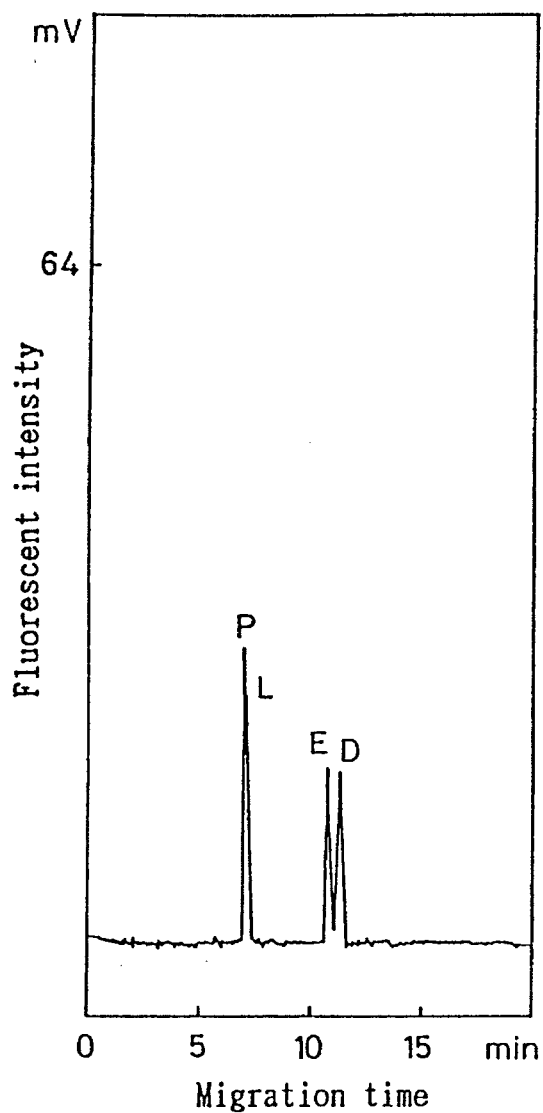
FIG. 8 shows the electrophoresis of dansyl amino acid in the case of using a microflow cell according to the present invention.

FIG. 8 shows the electrophoresis of dansyl amino acid. As the separation tube, a noncoated fused silica tube having an inner diameter of 50 μm and a length (effective length) of 300 mm was used. As the buffer liquid, sodium phosphate of 20 mM and a pH of 9.5 was used. About 12 nl of sample was introduced by a siphon to a depth of 15 cm in 10 seconds. The voltage applied was 10 kV and the current was about 11 μA. Detection was carried out at by projecting excited light having a wavelength of 330 nm and fluorescence emitting light having a wavelength of 530 nm.

As the sample, a 0.05 μg/ml of an aqueous solution of each of dansyl proline (P), dansyl leucine (L), dansyl glutamic acid (E) and dansyl aspartic acid (D) was used.

As is obvious from FIG. 8, the levels of the background signal and noise were low and the peak of each sample was distinct.

Wavelength Programming as Function of Time

Fluorescence detection is a detecting method for very selectively specifying the object of measurement by utilizing the fact that the wavelength of the excited light and wavelength of the fluorescence emitting light are respectively idiosyncratic. In order to detect a fluorescent substance under a certain optical condition, it is essential that the wavelength of the excited light is different from the wavelength of the measuring fluorescence emitting light.

Figure 9:
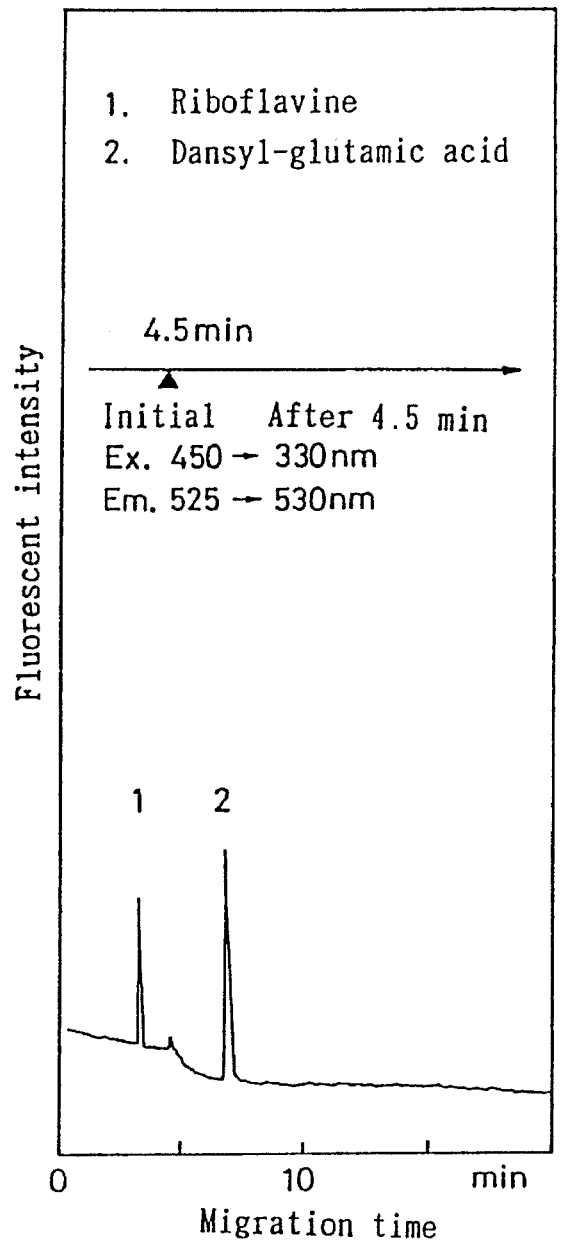
FIG. 9 shows the electrophoresis of a mixture of riboflavin and dansyl amino acid in the case of using a microflow cell using a microflow cell according to the present invention.

FIG. 9 shows the electrophoresis of riboflavin and dansyl amino acid. The wavelength of the excited light and the fluorescence emitting light were initially 450 nm and 525 nm, respectively, and they were changed to 330 nm and 530 nm after 4.5 minutes later. As the buffer liquid, sodium phosphate of 20 mM and a pH of 9.5 was used. About 12 nl of a mixed aqueous solution of 0.04 ng/ml of riboflavin and 0.2 mg/ml of dansyl amino acid was introduced as a sample by a siphon to a depth of 15 cm in 10 seconds. The voltage applied was 15 kV and the current was about 9 μA.

As is obvious from FIG. 9, riboflavin and dansyl amino acid were distinctly detected. The lower limit of riboflavin detection was 4 fmol. This value is about 8 times of the lower limit value of detection obtained by Fernandez and his co-worker by a fluorescence microscope. It is considered that the lower limit of detection can further be lowered by employing cut-off filters.

Measurement of Fluorescence Emitting Light Spectrum

The merit of use of a fluorescence spectrum detector is that it is possible to measure the fluorescence spectrum in order to identify the substance at the peak. If a laser is used as a light source, this is impossible.

Figure 10:
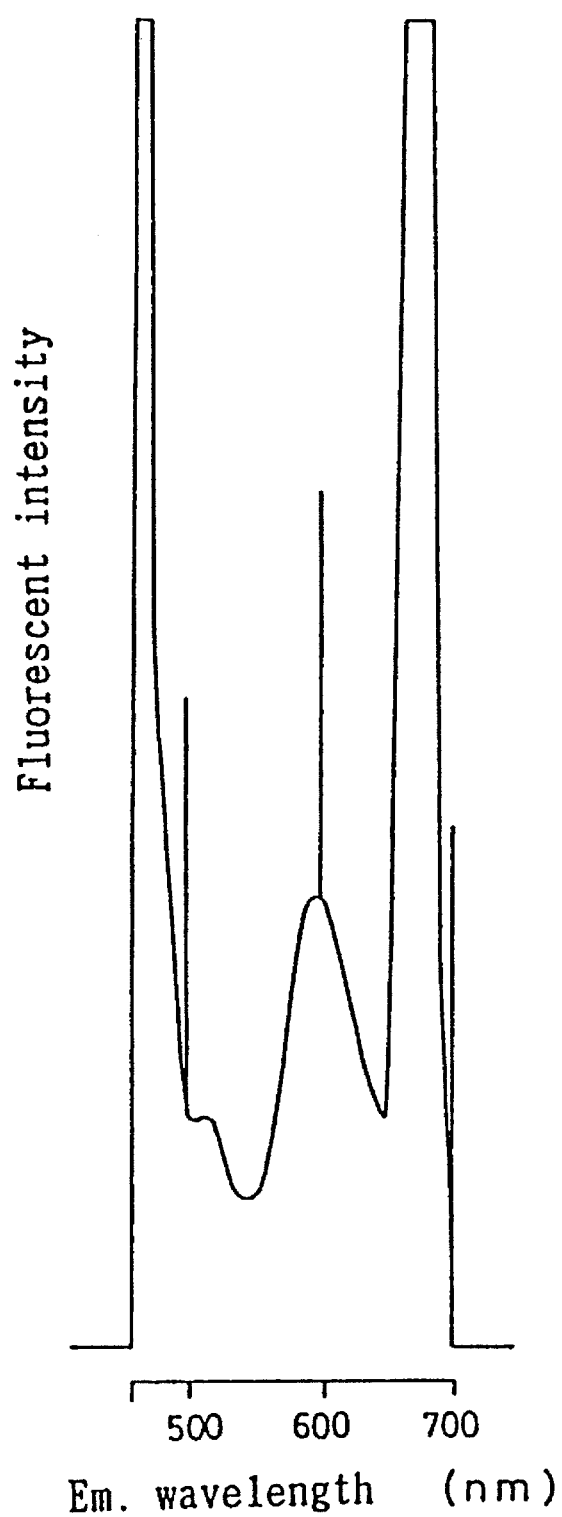
FIG. 10 shows the fluorescence spectrum of riboflavin obtained by using a stopped flow method while using a microflow cell according to the present invention.

FIG. 10 shows the spectrum of fluorescence emitting light of riboflavin obtained by measurement adopting a flow stopping method in which the application of a DC voltage is stopped during the scanning of the wavelength of fluorescence emitting light.

As shown in FIG. 10, a fluorescence spectrum is a spectrum intrinstic to each substance and provides very important information for identifying the substance.

As described above, a microflow cell of the present invention is very effective for fluoremetry in capillary electrophoresis. Wavelength programming for obtaining the maximum sensitivity and selectivity with respect to all the components of a sample mixture is possible. In addition, it is possible to measure a fluorescence spectrum in order to identify a component. Cut-off filters can be used in order to further enhance the sensitivity.

Although a microflow cell is applied to a capillary electrophoresis in this embodiment, it is also preferable to apply it to, for example, a fluorescence detector for microliquid chromatography.

The filling material inserted between the flow cell and the outer cylinder may be solid. The inner wall surface of the outer cylinder may be brought into close contact with the flow cell so as to utilize the inner wall itself as the filling material.

Figure 11:
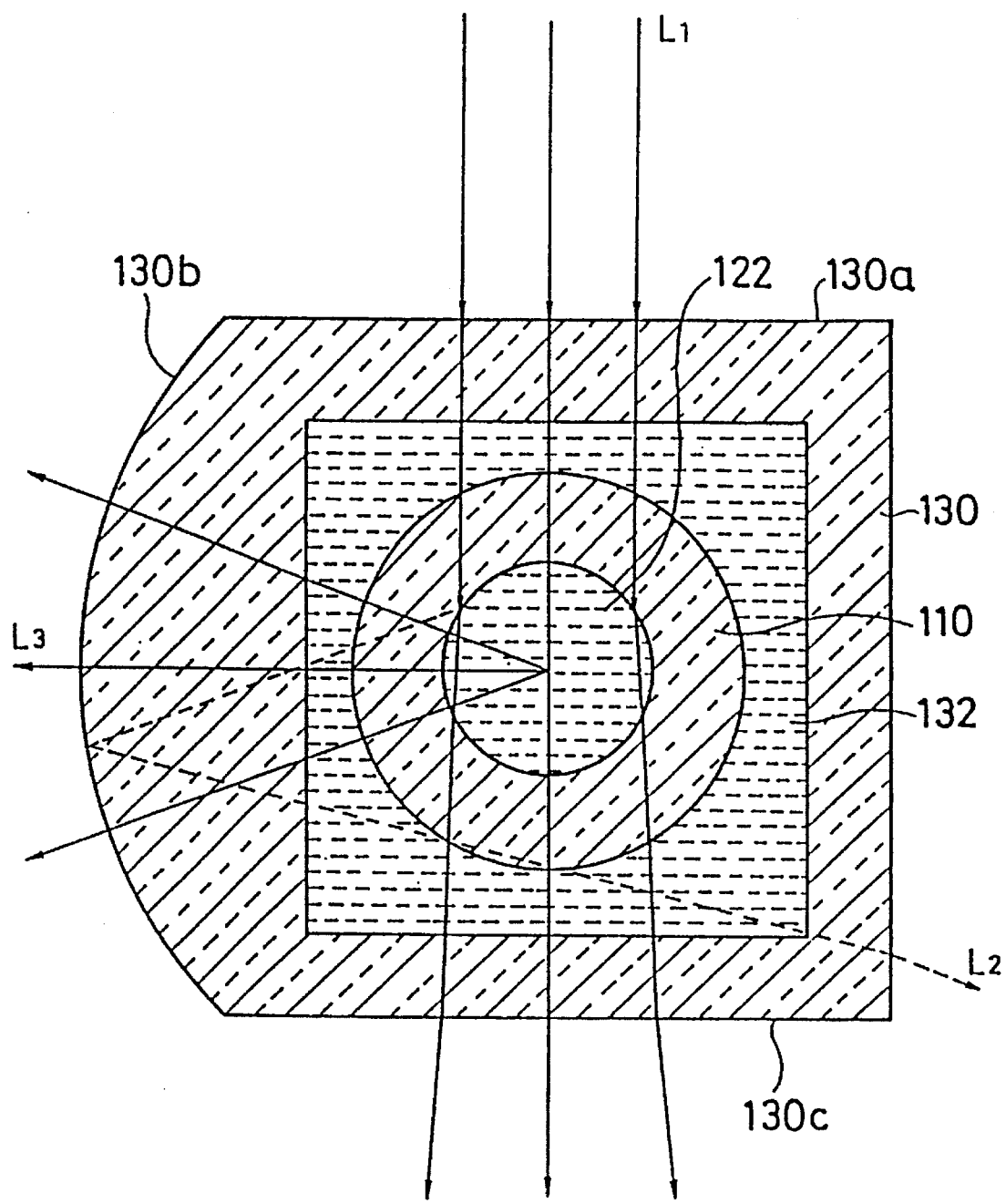
FIG. 11 is and explanatory view of another embodiment of a microflow cell according to the present invention.

FIG. 11 shows another embodiment of a microflow cell according to the present invention. The elements corresponding to those shown in FIG. 5 are indicated by the same numerals prefixed by the numeral 1.

In the microflow cell shown in FIG. 11, a light-emitting surface 130b of an outer cylinder 130 is concentric with a silica tube 110, thereby preventing the diffusion of the fluorescence emitting light $L_3$.

As described above, according to a microflow cell of the present invention, since an outer cylinder is provided on the outer periphery of a cylindrical flow cell and the gap between the flow cell and the outer cylinder is filled up with a filling liquid, the difference in the refractive index between the materials on both sides of the boundary is reduced, thereby reducing the quantity of scattered light.

While there has been described what is at present considered to be preferred embodiments of the invention, it will be understood that various modifications may be made thereto, and it is intended that the appended claims cover all such modifications as fall within the true spirit and scope of the invention.

What is claimed is:

1. A microflow cell for capillary electrophoresis and micro liquid chromatography comprising:

a circular cylindrical flow cell having an outer periphery and an inside surface;

a jacket disposed outside of said flow cell having flat exterior and interior surfaces on a light-entering face and a flat interior surface on a light-emitting face, said light-emitting face being at an angle of 90° with respect to excited light entering to said light-entering face;

a filling material inserted between said flow cell and said jacket having a refractive index substantially the same as said flow cell and said jacket;

an incoherent, changeable wavelength light source directed normal to said light-entering face; and a detector located to receive fluoresced light emitted from said light-emitting face.

2. A microflow cell according to claim 1, wherein said light-emitting face has a flat exterior surface parallel to the flat interior surface of said light-emitting face.

3. A microflow cell according to claim 1, wherein said light-emitting face has a cylindrical exterior surface concentric with said circular cylindrical flow cell.

4. A microflow cell for capillary electrophoresis and micro liquid chromatography comprising in combination:

an inner circular cylindrical capillary flow cell having an inner circular cylindrical surface and an outer circular cylindrical surface which is concentric with said inner cylindrical surface;

an outer cylinder disposed outside of said inner circular cylindrical flow cell having an inner surface and an outer surface, said outer cylinder inner surface having at least one flat light entering inner surface and a fluoresced light emitting outer surface;

a filling material inserted between said outer cylinder and said circular cylindrical flow cell;

wherein said fluoresced light emitting outer surface emits fluoresced light and is at an angle of 90° with respect to excited light entering said flat light entering surface; wherein said flat light; entering surface reduces scattered light and a detector located to receive light from said fluoresced light emitting outer surface.

5. A microflow cell according to claim 4, wherein the fluoresced light emitting outer surface of said outer cylinder has a flat outer surface for reducing scattered light at the time of emission.

6. A microflow cell according to claim 4, wherein said outer cylinder outer surface adjacent at an angle of 90° with respect to said light entering surface is concentric with said inner circular cylindrical flow cell.

7. A microflow cell according to claim 4, wherein said filling material is a liquid having a refractive index substantially the same as said flow cell and said light emitting outer surface.

8. A microflow cell according to claim 7, wherein said filling material is one selected from the group consisting of ethanol, propanol and dichrolomethane.

9. A microflow cell according to claim 4, further comprising a source of incoherent light which is directed to said outer cylindrical light entering inner surface.

10. A microflow cell in accordance with claim 4, wherein said fluoresced light emitting surface also emits scattered light which is noise of fluoresced detection.

11. A microflow cell in accordance with claim 4, wherein said fluoresced light emitting surface does not emit direct light from said light entering inner surface.

12. A capillary electrophoresis method comprising the steps of:

using an inner circular cylindrical capillary flow cell having an inner circular cylindrical surface and an outer circular cylindrical surface which is concentric with said inner cylindrical surface;

using an outer cylinder disposed outside of said inner circular cylindrical flow cell, said outer cylinder having an inner surface and an outer surface, said outer cylinder inner surface having at least one flat light entering inner surface and a fluoresced light emitting outer surface;

using a filling material inserted between said outer cylinder and said circular cylindrical flow cell;

wherein said fluoresced light emitting outer surface emits fluoresced light and is at an angle of 90° with respect to excited light entering said flat light entering surface;

wherein said flat light entering surface reduces scattered light; and using a detector located to receive light from said fluoresced light emitting outer surface.

13. A method according to claim 12, wherein the fluoresced light emitting outer surface of said outer cylinder has a flat outer surface for reducing scattered light at the time of emission.

14. A method according to claim 12, wherein said outer cylinder outer surface adjacent at an angle of 90° with respect to said light entering surface is concentric with said inner circular cylindrical flow cell.

15. A method according to claim 12, wherein said filling material is a liquid having a refractive index substantially the same as said flow cell and said light emitting outer surface.

16. A method according to claim 15, wherein said filling material is one selected from the group consisting of ethanol, propanol and dichrolomethane.

17. A method according to claim 12, further comprising a source of incoherent light which is directed to said outer cylindrical light entering inner surface.

18. A method in accordance with claim 12, wherein said fluoresced light emitting surface also emits scattered light which is noise of fluoresced detection.

19. A method in accordance with claim 12, wherein said fluoresced light emitting surface does not emit direct light from said light entering inner surface.

20. A method according to claim 12 wherein a fluorescence spectrum is measured.

21. A method for capillary electrophoresis and micro liquid chromatography comprising the steps of:

using a circular cylindrical flow cell having an outer periphery and an inside surface;

using a jacket disposed outside of said flow cell having flat exterior and interior surfaces on a light-entering face and a flat interior surface on a light-emitting face, said light-emitting face being at an angle of 90° with respect to excited light entering to said light-entering face;

using a filling material inserted between said flow cell and said jacket having a refractive index substantially the same as said flow cell and said jacket;

using an incoherent, changeable wavelength light source directed normal to said light-entering face; and using a detector located to receive fluoresced light emitted from said light-emitting face.

22. A method according to claim 21, wherein said light-emitting face has a flat exterior surface parallel to the flat interior surface of said light-emitting face.

23. A method according to claim 21, wherein said light-emitting face has a cylindrical exterior surface concentric with said circular cylindrical flow cell.

24. A method according to claim 21 wherein a fluorescence spectrum is measured.

* * * * *